United States Patent
Jung et al.

(10) Patent No.: US 11,000,989 B2
(45) Date of Patent: May 11, 2021

(54) METHOD FOR PREPARING A HIGHLY ELASTIC, BIODEGRADABLE, THREE-DIMENSIONAL STRUCTURE

(71) Applicant: KOREA INSTITUTE OF SCIENCE AND TECHNOLOGY, Seoul (KR)

(72) Inventors: Young Mee Jung, Seoul (KR); Soo Hyun Kim, Seoul (KR); Su Hee Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 489 days.

(21) Appl. No.: 15/786,686

(22) Filed: Oct. 18, 2017

(65) Prior Publication Data
US 2019/0111177 A1 Apr. 18, 2019

(30) Foreign Application Priority Data
Apr. 28, 2017 (KR) .................. 10-2017-0054897

(51) Int. Cl.
*B29C 64/314* (2017.01)
*B29C 64/106* (2017.01)
(Continued)

(52) U.S. Cl.
CPC ............ *B29C 64/106* (2017.08); *A61L 27/14* (2013.01); *A61L 27/18* (2013.01); *A61L 27/505* (2013.01);
(Continued)

(58) Field of Classification Search
CPC ..... B29C 64/10; B29C 64/106; B29C 64/112; B29C 64/118; B29C 64/209; B29C 64/307; B29C 64/314
See application file for complete search history.

(56) References Cited

U.S. PATENT DOCUMENTS 6,897,245 B2 * 5/2005 Gen .................. A61L 2/081
514/772.3
6,942,830 B2 * 9/2005 Mulhaupt ............. B29C 31/045
264/255
(Continued)

FOREIGN PATENT DOCUMENTS

CN    106349661 A  *  1/2017
CN    106433052 A  *  2/2017
(Continued)

OTHER PUBLICATIONS

Elomaa et al., Preparation of poly(ω-caprolactone)-based tissue engineering scaffolds by stereolithography, Acta Biomaterials 7 (2011) 3850-3856. (Year: 2011).*
(Continued)

*Primary Examiner* — Atul P. Khare
(74) *Attorney, Agent, or Firm* — Rabin & Berdo, P.C.

(57) ABSTRACT

A method for preparing a highly elastic biodegradable three-dimensional structure includes (a) mixing poly(lactide-co-ε-caprolactone) (PLCL) with at least one biocompatible heat stabilizer that is biocompatible with the PLCL, that is a heat stabilizer for the PLCL, and that is selected from the group consisting of α-tocopherol, barium-zinc, calcium-zinc, vitamin B, and combinations thereof to provide a solvent-free mixture; and (b) carrying out three-dimensional printing with the solvent-free mixture by heating the mixture at 150-250° C. for 5-20 minutes to provide a heated mixture; and ejecting the heated mixture through a nozzle. The three-dimensional structure maintains mechanical properties even after three-dimensional printing, by adding a biocompatible heat stabilizer to poly(L-lactide-co-ε-caprolactone). The three-dimensional structure is useful as a scaffold for tissue engineering.

10 Claims, 6 Drawing Sheets

Scale bar; 1cm

L=15mm
T=3mm

Scale bar; 1cm

Id=4mm
Od=8mm
L=15mm

Scale bar; 1cm d=8mm
L=10mm

(51) Int. Cl.
    *B33Y 80/00*     (2015.01)
    *A61L 27/14*     (2006.01)
    *A61L 27/58*     (2006.01)
    *A61L 31/14*     (2006.01)
    *C08G 63/08*     (2006.01)
    *C08K 5/00*      (2006.01)
    *C08K 3/08*      (2006.01)
    *B29C 64/209*    (2017.01)
    *B33Y 10/00*     (2015.01)
    *B33Y 70/00*     (2020.01)
    *C08K 5/1545*    (2006.01)
    *A61L 27/50*     (2006.01)
    *A61L 27/18*     (2006.01)

(52) U.S. Cl.
    CPC ............. *A61L 27/58* (2013.01); *A61L 31/143* (2013.01); *B29C 64/209* (2017.08); *B29C 64/314* (2017.08); *B33Y 10/00* (2014.12); *B33Y 70/00* (2014.12); *B33Y 80/00* (2014.12); *C08G 63/08* (2013.01); *C08K 3/08* (2013.01); *C08K 5/005* (2013.01); *C08K 5/1545* (2013.01); *C08K 2003/0893* (2013.01)

(56) References Cited

U.S. PATENT DOCUMENTS

| | | | | |
|---|---|---|---|---|
| 8,636,792 B2* | 1/2014 | Zheng | ............... | A61F 2/915 |
| | | | | 623/1.18 |
| 9,119,905 B2* | 9/2015 | Zheng | ............... | A61F 2/82 |
| 9,480,588 B2* | 11/2016 | Yan | ............... | A61B 90/39 |
| 9,703,819 B2* | 7/2017 | Chi | ............... | G06F 16/2228 |
| 9,855,156 B2* | 1/2018 | Yan | ............... | A61F 2/89 |
| 2007/0200268 A1* | 8/2007 | Dave | ............... | A61K 31/337 |
| | | | | 264/109 |
| 2008/0262146 A1* | 10/2008 | Yonezawa | ............... | C08J 5/18 |
| | | | | 524/560 |
| 2010/0197842 A1* | 8/2010 | Kamikawa | ............... | C08G 18/0895 |
| | | | | 524/195 |
| 2018/0370126 A1* | 12/2018 | Sawaguchi | ............... | B29B 13/06 |

FOREIGN PATENT DOCUMENTS

CN     106543662 A  *  3/2017
KR     101881087 B1 *  7/2018

OTHER PUBLICATIONS

K. Whang et al., "A novel method to fabricate bioabsorbable scaffolds", Polymer, 1995, pp. 837-842, vol. 36, No. 4.

Victor J. Chen et al., "Nano-fibrous poly ($_L$-lactic acid) scaffolds with interconnected spherical macropores", Biomaterials, 2004, pp. 2065-2073, vol. 25.

Dietmar W. Hutmacher, "Scaffolds in tissue engineering bone and cartilage", Biomaterials, 2000, pp. 2529-2543, vol. 21.

Achim Göpferich, "Mechanisms of polymer degradation and erosion", Biomaterials, 1996, pp. 103-114, vol. 17.

* cited by examiner

Scale bar; 1cm

L=15mm
T=3mm

Scale bar; 1cm

Id=4mm
Od=8mm
L=15mm

Scale bar; 1cm d=8mm
L=10mm

METHOD FOR PREPARING A HIGHLY ELASTIC, BIODEGRADABLE, THREE-DIMENSIONAL STRUCTURE

CROSS-REFERENCE TO RELATED APPLICATIONS

This application claims priority under 35 U.S.C. § 119 to Korean Patent Application No. 10-2017-0054897 filed on Apr. 28, 2017 in the Korean Intellectual Property Office, the disclosure of which is incorporated herein by reference in its entirety.

TECHNICAL FIELD

The following disclosure relates to a method for preparing a highly elastic biodegradable three-dimensional structure and a highly elastic biodegradable three-dimensional structure obtained thereby. More particularly, the following disclosure relates to a method for preparing a three-dimensional structure, which maintains mechanical properties even after three-dimensional printing, by adding a biocompatible heat stabilizer to poly(L-lactide-co-ε-caprolactone) and application of the three-dimensional structure to a scaffold for tissue engineering.

BACKGROUND

Tissue engineering is an academic field for restoring, regenerating or substituting damaged or failed tissues and organs by using the basic concept and technology of the existing science fields, such as life science, medical science and engineering science, so that they may conduct normal functions. In the traditional tissue engineering, a scaffold, cell and signal transfer are regarded as three main factors.

Conventional methods for processing a scaffold for tissue engineering include a salt leaching method which includes mixing with single-crystal salt, drying and dissolving salt into water, a phase separation method, a prototyping/solid preform structure, or the like [Non-Patent Document 1/Non-Patent Document 2/Non-Patent Document 3].

Recently, to overcome the limitation of the existing artificial scaffolds, 3D printing technology developed from rapid prototyping has been applied. Thus, it becomes possible to fabricate an artificial scaffold having a desired design and desired mechanical property values (porosity, interconnection among pores, or the like). 3D printing is classified into the three types of liquid-based, powder-based and solid-based 3D printing, depending on materials used therefor, and a typical example of each of the methods includes stereo lithography (SLA), selective laser sintering (SLS) and fused deposition modeling (FDM), respectively. Various other methods are also used. In general, a biodegradable polymer-based scaffold is obtained by using a method including applying heat to a polymer in an extrusion mode and carrying out ejection through a nozzle.

As materials for a scaffold for tissue engineering, biodegradable polymer materials have been used frequently and particular examples thereof include polycaprolactone, polyglycolide, polylactide, poly(lactide-co-glycolide) (PLGA) and poly(lactide-co-ε-caprolactone) (PLCL). Synthetic biodegradable polymers, such as polylactic acid (PLA) and poly(lactide-co-glycolide) (PLGA) have been approved of use in the human body by US Food and Drug Administration (FDA) and used as a scaffold. It is known that their degradation and degradation products conform to the general metabolic pathway [Non-Patent Document 4].

Currently, polycaprolactone and polylactide have been used frequently as 3D printing materials based on biodegradable polymers. Such materials are advantageous in that they are processed into filaments for 3D printing with ease and are ejected and stacked well during printing. Such materials have high mechanical properties, and thus have been used as a bone substitute for customized shaping of the contour of a patient's skull and face.

However, the application spectrum of various types of biodegradable polymers is not broad to date. Particularly, a highly elastic polymer, poly(lactide-co-ε-caprolactone), used frequently for regeneration of soft tissues has a difficulty in ejecting and stacking at low temperature due to the viscosity characteristics of the elastomer. When pressurizing the elastomer at high temperature in order to reduce the viscosity, it causes thermal degradation and undergoes significant deterioration of physical properties, and thus loses mechanical properties as an elastomer. As a result, currently, it has a limitation in application as a material for 3D printing.

REFERENCES

Non-Patent Documents

Non-Patent Document 1. Whang K, Thomas C H, Healy K E, Nuber G. Polymer 1995; 36:837

Non-Patent Document 2. Chen V J, Ma P X. Biomaterials 2004; 25:2065-73

Non-Patent Document 3. Hutmacher D W. Biomaterials 2000; 21:2529

Non-Patent Document 4. Gopferich A. Mechanisms of polymer degradation and erosion. Biomaterials 1996; 17:103-14

SUMMARY

The present disclosure is designed to solve the problems of the related art, and an embodiment of the present disclosure is directed to providing a method for preparing a three-dimensional structure, which maintains mechanical properties even after three-dimensional printing, by adding a biocompatible heat stabilizer to poly(L-lactide-co-ε-caprolactone), and a scaffold for tissue engineering using the biodegradable three-dimensional structure.

In one aspect, there is provided a method for preparing a biodegradable three-dimensional structure, which includes the steps of: (a) mixing poly(lactide-co-ε-caprolactone) (PLCL) with at least one biocompatible heat stabilizer selected from α-tocopherol, barium-zinc, calcium-zinc and vitamin B; and (b) carrying out three-dimensional printing with the mixture.

The PLCL may have a molar ratio of L-lactide to ε-caprolactone of 4-6:6-4, a number average molecular weight of 100000-300000, and a weight average molecular weight of 200000-600000.

The biocompatible heat stabilizer may be α-tocopherol.

The biocompatible heat stabilizer may be mixed in an amount of 0.001-2 wt % based on the weight of the PLCL.

The three-dimensional printing may be carried out by heating the mixture at 150-250° C. for 5-20 minutes and then ejecting the mixture through a nozzle.

The ejection may be carried out under a pneumatic pressure of 600-900 kPa.

The biocompatible heat stabilizer may be α-tocopherol; the PLCL may have a molar ratio of L-lactide to ε-caprolactone of 4.5-5.5:5.5-4.5, a number average molecular weight of 100000-300000, and a weight average molecular weight of 200000-600000; the biocompatible heat stabilizer may be mixed in an amount of 0.1-0.5 wt % based on the weight of the PLCL; the organic solvent may be mixed in an amount of 0.0005-0.002 wt % based on the weight of the PLCL; and the three-dimensional printing may be carried out by heating the mixture at 200-230° C. for 10-20 minutes and then ejecting the mixture through a nozzle under a pneumatic pressure of 600-900 kPa.

According to the present disclosure, it is possible to provide a biodegradable three-dimensional structure which maintains mechanical properties even after three-dimensional printing by adding a biocompatible heat stabilizer to poly(lactide-co-ε-caprolactone), and to provide a scaffold for tissue engineering using the biodegradable three-dimensional structure.

DETAILED DESCRIPTION OF EMBODIMENTS

Figure 1:
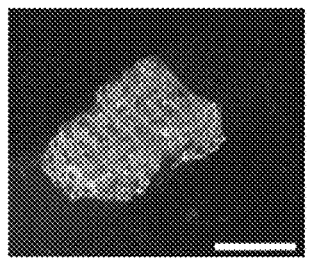
FIG. 1 shows various types of images of the biodegradable three-dimensional structures obtained from Example 1 according to the present disclosure.
Figure 1:
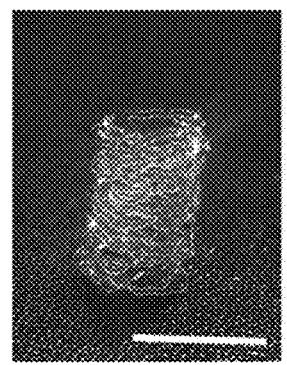
Figure 1:
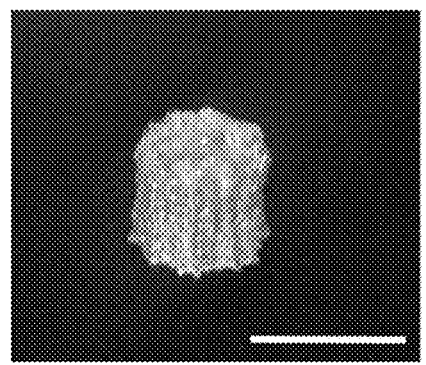

Hereinafter, various aspects and embodiments of the present disclosure will be explained in more detail.

In one aspect, there is provided a method for preparing a biodegradable three-dimensional structure, which includes the steps of: (a) mixing poly(lactide-co-ε-caprolactone) (PLCL) with at least one biocompatible heat stabilizer selected from α-tocopherol, barium-zinc, calcium-zinc and vitamin B; and (b) carrying out three-dimensional printing with the mixture.

According to the related art, polycaprolactone and polylactide have been used easily as biodegradable polymers for three-dimensional printing. In addition, PLCL, a highly elastic biodegradable polymer used frequently for regenerating soft tissues, has high viscosity and thus shows a difficulty in ejecting and stacking at low temperature. Moreover, there is a problem in that PLCL causes thermal degradation, and undergoes deterioration of physical properties and loses mechanical properties as an elastomer, when it is pressurized at a high temperature of 75° C. or higher in order to reduce the viscosity. To solve the above-mentioned problem, according to the present disclosure, a biocompatible heat stabilizer is added to prevent thermal degradation of PLCL so that a decrease in molecular weight occurring after a thermal printing process may be reduced and highly elastic mechanical properties may be retained.

The organic solvent may be at least one selected from tetrahydrofuran, dimethyl formamide, diethyl formamide, N-methyl-2-pyrrolidone, dimethyl sulfoxide, dimethyl acetamide, methanol, ethanol, chloroform and dichloromethane, but is not limited thereto. Preferably, the organic solvent may be tetrahydrofuran.

The PLCL may have a molar ratio of L-lactide to ε-caprolactone of 4-6:6-4, a number average molecular weight of 100000-300000, and a weight average molecular weight of 200000-600000. When the PLCL satisfies the above-defined range of molar ratio, number average molecular weight and weight average molecular weight, it has highly elastic mechanical properties and a glass transition temperature (Tg) of −20 to 0° C. Thus, the PLCL has physical properties as an elastomer at room temperature, and shows flexibility in its polymer chain under heating so that it may have decreased viscosity to allow ejection through a three-dimensional printing nozzle.

The biocompatible heat stabilizer may be α-tocopherol. Particularly, when using α-tocopherol as a biocompatible heat stabilizer, it is shown that the elastic modulus and elongation of the biodegradable three-dimensional structure produced by a thermal three-dimensional printing process are improved significantly as compared to those before three-dimensional printing. In addition, α-tocopherol has no cytotoxicity and causes no inflammation response, and thus allows three-dimensional printing while maintaining biocompatibility.

The biocompatible heat stabilizer may be mixed in an amount of 0.001-2 wt % based on the PLCL. Even when the biocompatible heat stabilizer is added in such a small amount, it is possible to prevent thermal degradation. When the biocompatible heat stabilizer is added in an amount less than the lower limit, it is not possible to provide a sufficient effect of preventing thermal degradation. When the biocompatible heat stabilizer is added in an amount larger than the upper limit, it is used in an excessive amount undesirably to cause low cost-efficiency.

The three-dimensional printing may be carried out by heating the mixture at 150-250° C. for 5-20 minutes and ejecting the mixture through a nozzle, and the ejection may be carried out under a pneumatic pressure of 600-900 kPa.

Although it is not stated specifically in the following Examples and Comparative Examples, various types of biocompatible heat stabilizers were determined for the distortion strength of each of the resultant biodegradable three-dimensional structures obtained by varying the molar ratio of L-lactide to ε-caprolactone, number average molecular weight and weight average molecular weight of PLCL, ratio of the biocompatible heat stabilizer based on PLCL, ratio of the organic solvent based on PLCL, and heating temperature and time and ejection pressure of PLCL and the biocompatible heat stabilizer, during the preparation of the biodegradable three-dimensional structures through three-dimensional printing using the mixture of the PLCL with the biocompatible heat stabilizer. In addition, the external surface roughness was determined through scanning electron microscopy (SEM).

As a result, when all of the following conditions were satisfied, the three-dimensional structure was not broken even after measuring distortion strength 300 times, had a significantly smooth initial external surface roughness and caused no change and defect in external surface roughness even after measuring distortion strength 300 times, unlike the other types of biocompatible heat stabilizers and the other numeral ranges.

However, when any one of the following conditions is not satisfied, a failure occurred after determining distortion strength and a significant defect and change in external surface roughness were observed.

(i) the biocompatible heat stabilizer is α-tocopherol, (ii) the molar ratio of L-lactide to ε-caprolactone in PLCL is 4.5-5.5:5.5-4.5, (iii) PLCL has a number average molecular weight of 100000-300000, (iv) PLCL has a weight average molecular weight of 200000-600000, (v) the ratio of the biocompatible heat stabilizer based on PLCL is 0.1-0.5 wt %, (vi) the ratio of the organic solvent based on PLCL is 0.0005-0.002 wt %, (vii) the heating temperature of the PLCL and the biocompatible heat stabilizer is 200-230° C., (viii) the heating time of the PLCL and the biocompatible heat stabilizer is 10-20 minutes, and (ix) the ejection pressure is 600-900 kPa.

The preparation examples and examples will now be described in detail with reference to the accompanying drawings. The following preparation examples and examples are for illustrative purposes only and not intended to limit the scope of this disclosure.

Example 1: Preparation of Biodegradable Three-Dimensional Structure

First, 800 mg of poly(L-lactide-co-ε-caprolactone) having a number average molecular weight of 163000 and a weight average molecular weight of 215000 was cut into a size of 5 mm or less, and then mixed homogeneously with a solution obtained by dissolving 0.2% of α-tocopherol based on the weight of the copolymer in 800 μL of tetrahydrofuran to obtain a mixture. Then, the mixture was introduced to a 10 mL-sized dispenser in a three-dimensional printer system, the dispenser was heated at 210° C. for 15 minutes, and then the mixture was ejected under a pneumatic pressure of 860 kPa to provide a biodegradable three-dimensional structure.

Example 2: Preparation of Biodegradable Three-Dimensional Structure

A biodegradable three-dimensional structure was obtained in the same manner as Example 1, except that α-tocopherol was used in an amount of 0.02% based on the copolymer.

Comparative Example 1

A biodegradable three-dimensional structure was obtained in the same manner as Example 1, except that the solution containing the biocompatible heat stabilizer (α-tocopherol) dissolved in tetrahydrofuran was not mixed with the copolymer but the copolymer was subjected to three-dimensional printing.

FIG. 1 shows various types of images of the biodegradable three-dimensional structures obtained from Example 1 according to the present disclosure.

As can be seen from FIG. 1, it is possible to obtain various types of biodegradable three-dimensional structures by using a mixture of PLCL with α-tocopherol.

Figure 2:
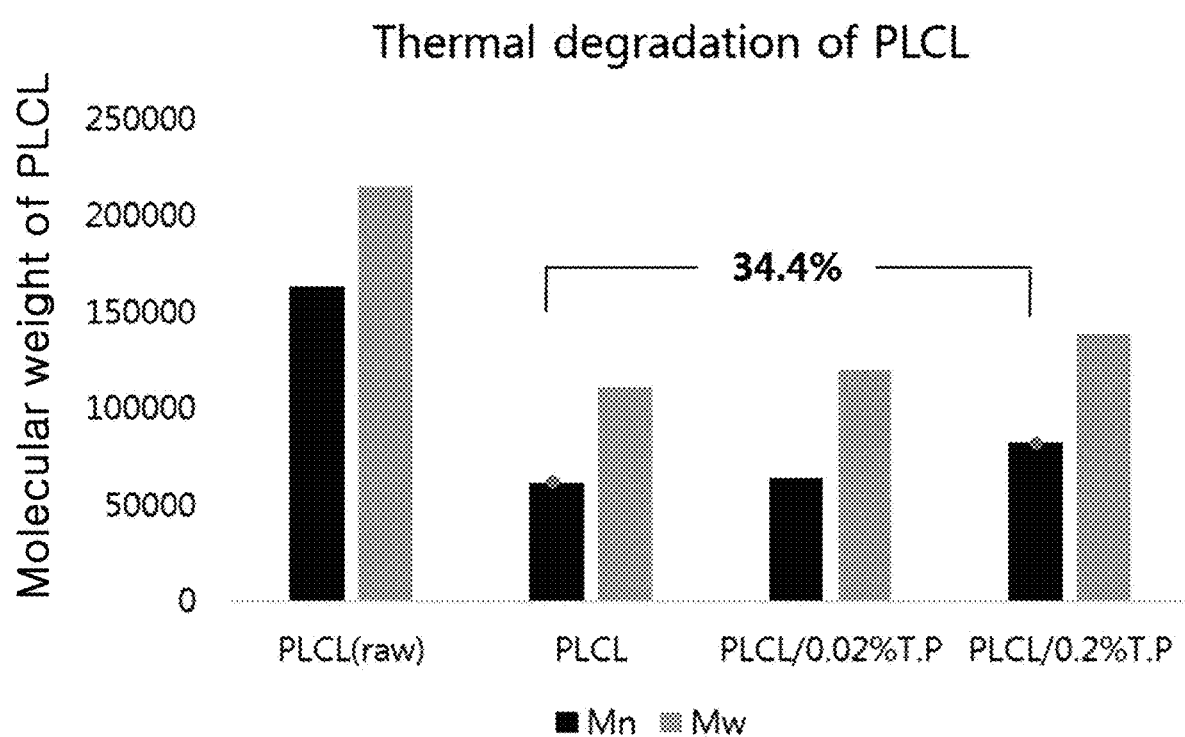
FIG. 2 is a graph illustrating the number average molecular weight (Mn) and weight average molecular weight (Mw) of each of the biodegradable three-dimensional structures according to Examples 1 and 2, and the biodegradable three-dimensional structure according to Comparative Example 1, before and after three-dimensional printing.

FIG. 2 is a graph illustrating the number average molecular weight (Mn) and weight average molecular weight (Mw) of each of the biodegradable three-dimensional structures according to Examples 1 and 2, and the biodegradable three-dimensional structure according to Comparative Example 1, before and after three-dimensional printing.

Referring to FIG. 2, it can be seen that addition of α-tocopherol leads to a decrease in molecular weight reduction by 37.42% as compared to the biodegradable three-dimensional structure to which no α-tocopherol is added.

Figure 3A:
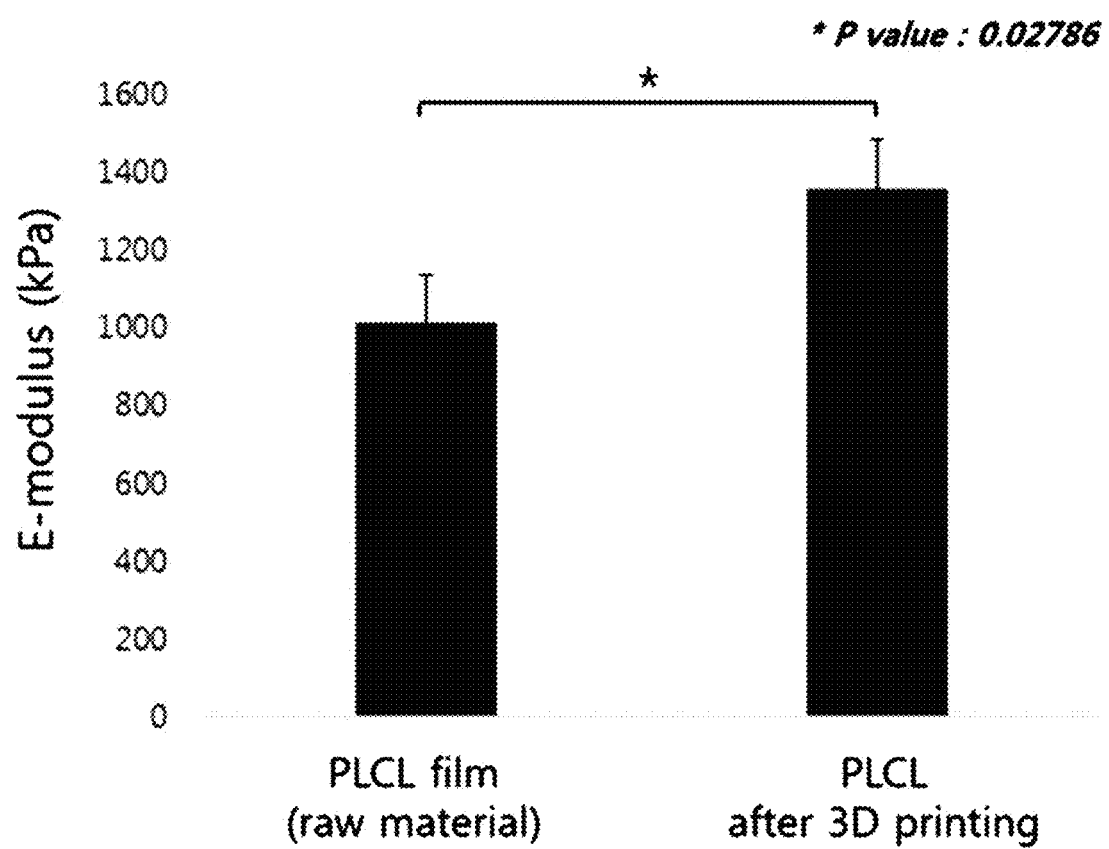
FIGS. 3A and 3B are graphs illustrating E-modulus and elongation of the biodegradable three-dimensional structure obtained from Example 1 according to the present disclosure, before and after three-dimensional printing.
Figure 3B:
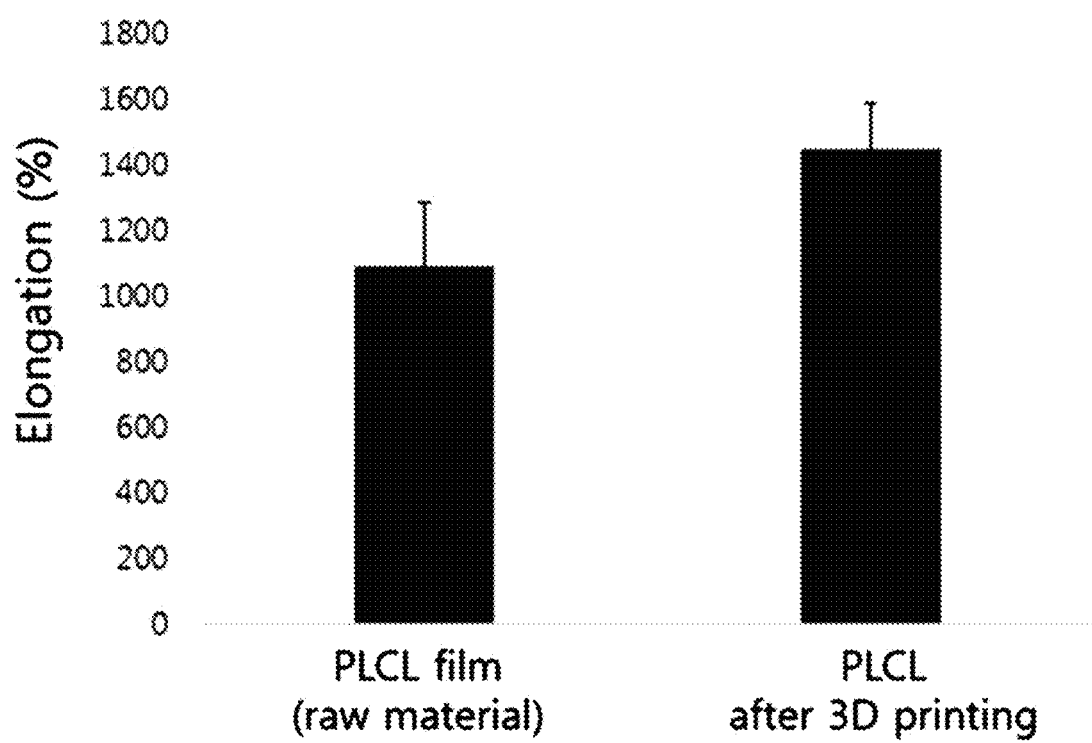

FIGS. 3A and 3B are graphs illustrating E-modulus and elongation of the biodegradable three-dimensional structure obtained from Example 1 according to the present disclosure, before and after three-dimensional printing.

Referring to FIGS. 3A and 3B, it can be seen that when α-tocopherol is added to PLCL, the mechanical properties of a flexible material are retained in terms of the value of E-modulus and elongation even after three-dimensional printing.

Figure 4:
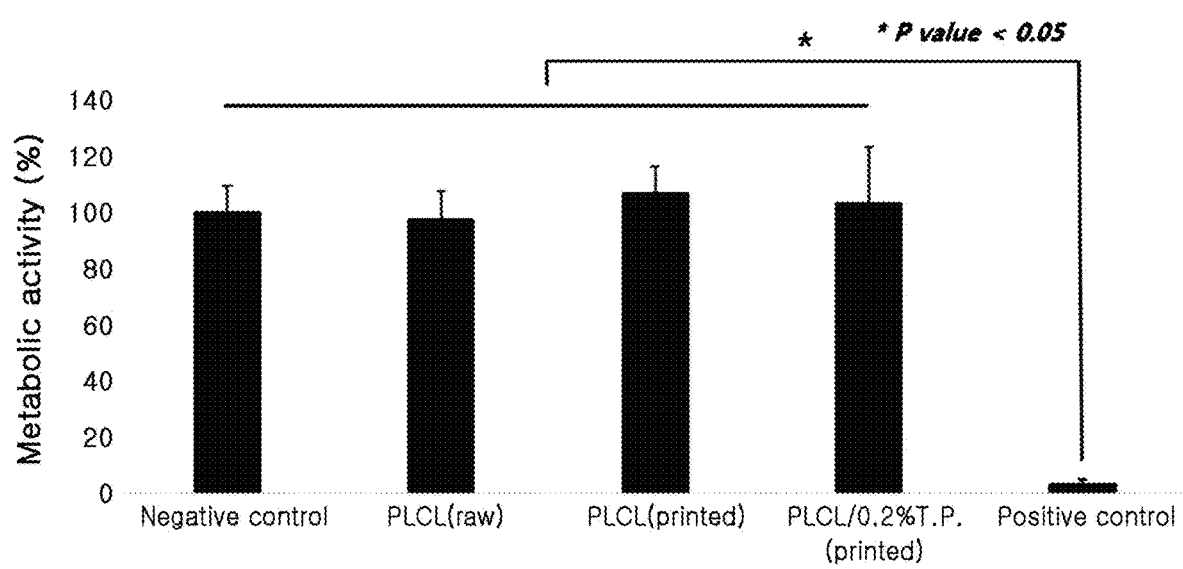
FIG. 4 is a graph illustrating the results of a cytotoxicity test for the biodegradable three-dimensional structure obtained from Example 1 according to the present disclosure.

FIG. 4 is a graph illustrating the results of a cytotoxicity test for the biodegradable three-dimensional structure obtained from Example 1 according to the present disclosure.

Referring to FIG. 4, the PLCL material containing α-tocopherol shows no cytotoxicity like the negative control.

Figure 5:
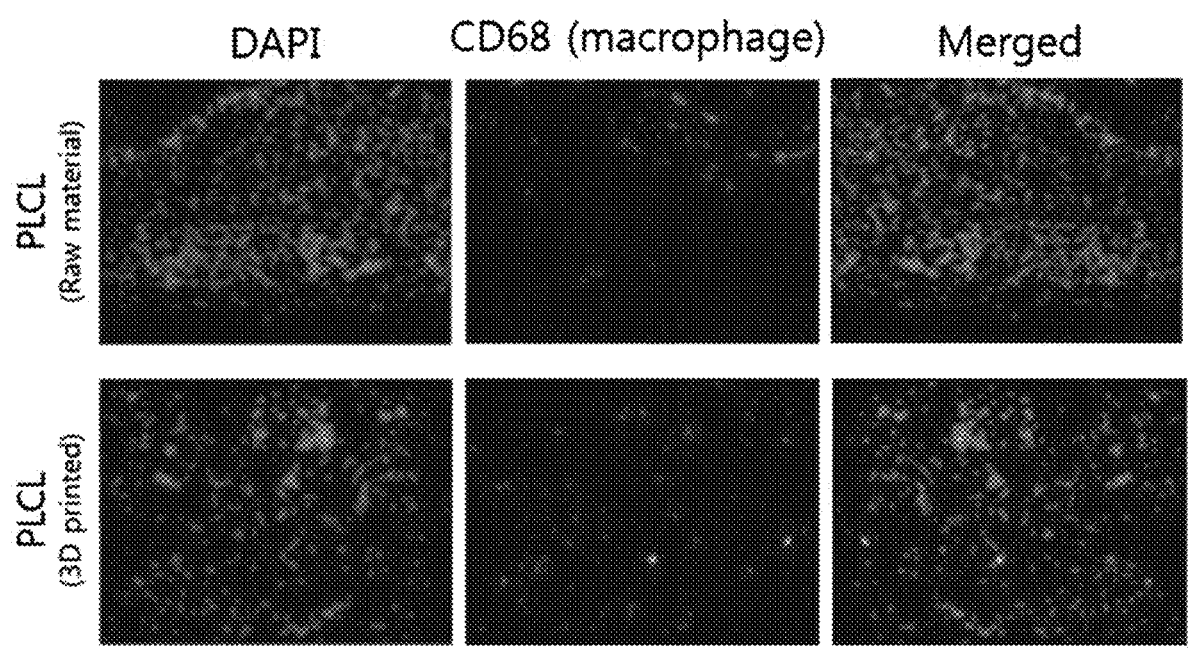
FIG. 5 is an image illustrating the results of an in vivo inflammation response test for the biodegradable three-dimensional structure obtained from Example 1 according to the present disclosure.

FIG. 5 is an image illustrating the results of an in vivo inflammation response test for the biodegradable three-dimensional structure obtained from Example 1 according to the present disclosure.

Referring to FIG. 5, when the introduction of macrophages is identified at the subcutaneous site of an animal, a similar amount of expression of macrophage markers is observed in the PLCL three-dimensional structure containing α-tocopherol and the raw material, PLCL. After checking the amount, it is shown that the amount is merely a degree of response appearing in the initial stage after transplantation. Thus, it can be stated that the PLCL three-dimensional structure containing α-tocopherol causes no inflammation response.

As a result, according to the present disclosure, it is possible to provide a biodegradable three-dimensional structure, which maintains mechanical properties even after three-dimensional printing, by adding a biocompatible heat stabilizer to polyp lactide-co-ε-caprolactone), and to apply the biodegradable three-dimensional structure to a scaffold for tissue engineering.

What is claimed is:

1. A method for preparing a biodegradable, three-dimensional structure, the method comprising:
   (a) mixing poly(lactide-co-ε-caprolactone) (PLCL) with at least one biocompatible heat stabilizer that is biocompatible with the PLCL, that is a heat stabilizer for the PLCL, and that is selected from the group consisting of α-tocopherol, barium-zinc, calcium-zinc, vitamin B, and combinations thereof to provide a solvent-free mixture; and
   (b) carrying out three-dimensional printing of the solvent-free mixture by heating the mixture at 150-250° C. for 5-20 minutes to provide a heated mixture, and ejecting the heated mixture through a nozzle, said heating decreasing viscosity of the PLCL so as to permit said ejecting, and said at least one biocompatible heat stabilizer permitting said decrease in viscosity without substantially thermally degrading the PLCL.

2. The method for preparing a biodegradable, three-dimensional structure according to claim 1, wherein the PLCL has a molar ratio of L-lactide to ε-caprolactone of 4-6:6-4, a number average molecular weight of 100,000-300,000, and a weight average molecular weight of 200,000-600,000.

3. The method for preparing a biodegradable, three-dimensional structure according to claim 2, wherein the at least one biocompatible heat stabilizer is α-tocopherol.

4. The method for preparing a biodegradable, three-dimensional structure according to claim 1, wherein the at least one biocompatible heat stabilizer is mixed in an amount of 0.001-2 wt % based on weight of the PLCL.

5. The method for preparing a biodegradable, three-dimensional structure according to claim 1, wherein said ejecting of the heated mixture is carried out under a pneumatic pressure of 600-900 kPa.

6. The method for preparing a biodegradable, three-dimensional structure according to claim 1, wherein:
the at least one biocompatible heat stabilizer is α-tocopherol;
the PLCL has a molar ratio of L-lactide to ε-caprolactone of 4.5-5.5:5.5-4.5, a number average molecular weight of 100,000-300,000, and a weight average molecular weight of 200,000-600,000;
the ε-tocopherol is mixed in an amount of 0.1-0.5 wt % based on weight of the PLCL; and
carrying out the three-dimensional printing comprises heating the solvent-free mixture at 200-230° C. for 10-20 minutes to provide the heated mixture; and ejecting the heated mixture through the nozzle under a pneumatic pressure of 600-900 kPa.

7. A method for preparing a biodegradable, three-dimensional structure, the method comprising:
(a) mixing poly(lactide-co-ε-caprolactone) (PLCL) with an organic solvent and a biocompatible heat stabilizer that is biocompatible with the PLCL, that is a heat stabilizer for the PLCL, and that is selected from α-tocopherol to provide a mixture; and
(b) carrying out three-dimensional printing of the mixture by heating the mixture at 200-230° C. for 10-20 minutes to provide a heated mixture, and ejecting the heated mixture through a nozzle, said heating decreasing viscosity of the PLCL for said ejecting, and said at least one biocompatible heat stabilizer permitting said decrease in viscosity without thermally degrading the PLCL,
wherein:
the PLCL has a molar ratio of L-lactide to ε-caprolactone of 4.5-5.5:5.5-4.5, a number average molecular weight of 100,000-300,000, and a weight average molecular weight of 200,000-600,000;
the α-tocopherol is mixed in an amount of 0.1-0.5 wt % based on weight of the PLCL;
the organic solvent is mixed in an amount of 0.0005-0.002 wt % based on weight of the PLCL; and
ejecting the heated mixture through the nozzle is carried out under a pneumatic pressure of 600-900 kPa.

8. The method for preparing a biodegradable, three-dimensional structure according to claim 7, wherein the biocompatible heat stabilizer further comprises at least one of barium-zinc, calcium-zinc, and vitamin B.

9. The method for preparing a biodegradable, three-dimensional structure according to claim 7, wherein the organic solvent is selected from the group consisting of tetrahydrofuran, dimethyl formamide, diethyl formamide, N-methyl-2-pyrrolidone, dimethyl sulfoxide, dimethyl acetamide, methanol, ethanol, chloroform, dichloromethane, and combinations thereof.

10. The method for preparing a biodegradable, three-dimensional structure according to claim 7, wherein the organic solvent is tetrahydrofuran.

* * * * *